018
United States Patent [19]

Nakanishi

[11] 4,105,668

[45] Aug. 8, 1978

[54] PROCESS FOR 6-AMINO-2,2-DIMETHYL-3-(5-TETRAZOLYL)PENAM

[75] Inventor: Susumu Nakanishi, Niantic, Conn.

[73] Assignee: Pfizer Inc., New York, N.Y.

[21] Appl. No.: 790,021

[22] Filed: Apr. 22, 1977

Related U.S. Application Data

[63] Continuation-in-part of Ser. No. 540,127, Jan. 10, 1975, abandoned.

[51] Int. Cl.$^2$ ............................................. C07D 499/08
[52] U.S. Cl. ............................ 260/306.7 R; 260/239.1
[58] Field of Search ................... 260/306.7 C, 306.7 R

[56] References Cited

PUBLICATIONS

*Chemical Abstracts,* 68:222318, (1968).

*Primary Examiner*—Nicholas S. Rizzo
*Attorney, Agent, or Firm*—Connolly and Hutz

[57] ABSTRACT

Certain 6-amino-2,2-dimethyl-3-(1-substituted tetrazol-5-yl)penam and 6-(protected amino)-2,2-dimethyl-3-(1-substituted tetrazolyl-5-yl)penam compounds react with hydrogen fluoride to produce 6-amino-2,2-dimethyl-3-(5-tetrazolyl)penam, a useful intermediate for the synthesis of antibacterial agents.

10 Claims, No Drawings

PROCESS FOR 6-AMINO-2,2-DIMETHYL-3-(5-TETRAZOLYL)PENAM

CROSS-REFERENCE TO RELATED APPLICATIONS

This application is a continuation-in-part of application Ser. No. 540,127 filed Jan. 10, 1975 and now abandoned.

BACKGROUND OF THE INVENTION

This invention relates to a new chemical process for the preparation of 6-amino-2,2-dimethyl-3-(5-tetrazolyl)penam. Said 6-amino-2,2-dimethyl-3-(5-tetrazolyl)penam is valuable in the art as a chemical intermediate, since acylation thereof produces 6-acylamino-2,2-dimethyl-3-(5-tetrazolyl)penam compounds, which are useful antibacterial agents. The process of the invention involves treating certain 6-amino-2,2-dimethyl-3-(5-tetrazolyl)penam and 6-(protected amino)-2,2-dimethyl-3-(5-tetrazolyl)penam compounds, bearing an appropriate substituent at the 1-position of the tetrazole ring, with hydrogen fluoride.

It is known that 6-amino-2,2-dimethyl-3-(5-tetrazolyl)penam can be prepared from the same compounds which act as starting materials for the process of the instant invention, by treatment by trifluoroacetic acid. However, the instant process produces a higher yield of higher purity product, and it is considerably more convenient to operate when working on a large scale.

SUMMARY OF THE INVENTION

According to the invention there is provided a novel process for the preparation of 6-amino-2,2-dimethyl-3-(5-tetrazolyl)penam, and the acid-addition salts thereof, which comprises reacting a compound of formula:

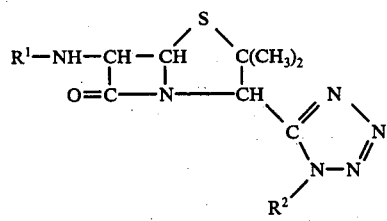

or an acid-addition salt thereof, with hydrogen fluoride, at a temperature within the range from about −20° C. to about 20° C;
wherein
$R^1$ is selected from the group consisting of hydrogen and

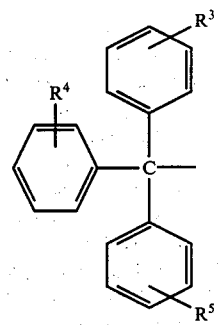

wherein
$R^3$, $R^4$, and $R^5$ are each selected from the group consisting of hydrogen, fluoro, chloro, bromo, alkyl having from one to four carbon atoms, alkoxy having from one to four carbon atoms and phenyl; and $R^2$ is selected from the group consisting of

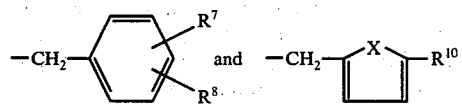

wherein
$R^7$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, benzyloxy and phenyl;
$R^8$ is selected from the group consisting of hydrogen, hydroxy, fluoro, chloro, unbranched-alkyl having from one to six carbon atoms and unbranched-alkoxy having from one to six carbon atoms;
$R^{10}$ is selected from the group consisting of hydrogen and methyl;
and X is selected from the group consisting of oxygen and sulfur;
provided that at least one of $R^7$ and $R^8$ is selected from the group consisting of 2-hydroxy, 4-hydroxy, 4-alkoxy having from one to six carbon atoms, 2-(unbranched-alkoxy) having from one to six carbon atoms and 4-benzyloxy.

DETAILED DESCRIPTION OF THE INVENTION

The starting materials and the product of this invention are identified as derivatives of "penam" which has been defined by Sheehan et. al., in the *Journal of the American Chemical Society*, 75, 3293 (1953), as referring to the structure:

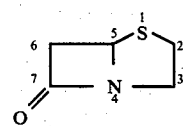

Although the term penam does not normally carry any stereochemical implications, the stereochemistry of the penam compounds of the instant invention corresponds to that found in the naturally-occurring penicillins. Using this terminology, the well-known antibiotic penicillin G (benzylpenicillin) is designated as 6-(2- phenylacetamido)-2,2-dimethylpenam-3-carboxylic acid.

The process of this invention is normally carried out by contacting a compound of formula I, wherein $R^1$ and $R^2$ are as previously defined, with hydrogen fluoride, at a temperature in the range from about $-20°$ C. to about $20°$ C., and preferably from $-5°$ C. to $5°$ C., until conversion into product is substantially complete. The time course of the reaction varies according to a number of factors, such as the reaction temperature and the reactivity of the particular substrate. In particular, the reaction proceeds faster at higher temperatures, whereas at lower temperatures it takes a longer time to complete the conversion to product. However, when working in the temperature range from $-5°$ C. to $5°$ C., reaction times of from about 0.5 to about three hours are typically used.

Although when carrying out the process of this invention, it is common to react the said compound of formula I with hydrogen fluoride alone, various co-solvents can be added to the reaction medium. Any co-solvent which is miscible with the hydrogen fluoride and which does not adversely interact with the starting material or the product, can be added, and typical examples of co-solvents are: lower alkanoic acids, such as formic acid and acetic acid; lower alkanoic esters, such as methyl acetate and ethyl acetate; chlorinated hydrocarbons such as dichloromethane and dichloroethane; ethers such as dioxane and 1,2-dimethoxyethane; acetonitrile; lower nitroalkanes, such as nitromethane and nitroethane; sulfones such as dimethyl sulfone and sulfolane; sulfur dioxide; and mixtures thereof. However, it is preferable to limit the volume of co-solvent to an amount equal to or less than the volume of hydrogen fluoride used. Moreover, it is usual to chose reaction conditions which are substantially homogeneous.

Although this is not essential for the success of the reaction, it is often advantageous, from the standpoint of speeding up the rate of reaction and of obtaining a good yield of high purity product, to add to the reaction medium a carbonium ion trapping agent. Typical carbonium ion traps which can be used include hydroxy- and alkoxy-substituted aromatic compounds, such as phenol, $\alpha$- and $\beta$-naphthol, anisole, phenetole, veratrole and $\alpha$- and $\beta$-methoxynaphthalene. The amount of carbonium ion trapping agent added is usually at least one molar equivalent, based on the amount of the compound of formula I, but amounts larger than one molar equivalent are often used. However, the volume of added trapping agent will not normally be greater than the volume of hydrogen fluoride used. If both a co-solvent and a carbonium ion trapping agent are used, their combined volume will not normally be greater than the volume of hydrogen fluoride used. A particularly convenient trapping agent is anisole.

When carrying out the process of the invention, it is preferable to use an excess of hydrogen fluoride. Although an excess of as low as five molar equivalents will successfully lead to the formation of product, it is usually preferable to use at least twenty molar equivalents of hydrogen fluoride. In many instances, excesses up to about two hundred molar equivalents are used. In those cases wherein the hydrogen fluoride is used in the absence of a co-solvent, it is convenient to use the hydrogen fluoride in an amount necessary to substantially dissolve the starting reagent of formula I.

The compounds of formula I, wherein $R^1$ is hydrogen, are of course basic, and as such they will form acid-addition salts. Both the free base form, and all the acid-addition salts, of the compounds of formula I can serve as starting materials in the process of this invention. The said acid-addition salts are prepared in conventional fashion. A typical method involves contacting equimolar proportions of the free base form of the compound of formula I, wherein $R^1$ is hydrogen, and the requisite acid, in an appropriate solvent, at about $0°$ C. Appropriate solvents are, for example, ethers, such as diethyl ether, 1,2-dimethoxyethane and tetrahydrofuran, chlorinated hydrocarbons, such as chloroform and methylene chloride, acetone and water. Salt formation takes place rapidly, and the acid-addition salt can be recovered by evaporation of the solvent, or by precipitation using a non-solvent followed by filtration. Typical examples of salts which can be used are: sulfate, hydrochloride, hydrofluoride, nitrate, phosphate perchlorate, acetate, chloroacetate, dichloroactate, trichloroacetate, fluoroacetate, difluoroacetate, trifluoroacetate, lactate, tartrate, citrate, benzoate, picrate and sulfonates such as the methanesulfonate, benzenesulfonate and p-toluenesulfonate.

The 6-amino-2,2-dimethyl-3-(5-tetrazolyl)penam produced by this process can be isolated readily and easily by standard methods. For example, particularly when operating on a small scale, it is often convenient to recover the product from the reaction mixture simply by removal of all volatile components by evaporation in vacuo. Alternatively, the product can often be induced to precipitate by the addition of a large excess of a solvent in which the product is insoluble, such as diethyl or diisopropyl ether, and then the product can be recovered by filtration. As will be appreciated by one skilled in the art, in those cases wherein the starting material is used in the form of an acid-addition salt, the above isolation techniques normally lead to recovery of the product as the corresponding acid-addition salt. However, this acid-addition salt is then converted into 6-amino-2,2-dimethyl-3-(5-tetrazolyl)penam by neutralization (basification), using standard methods, before acylation. Moreover, the initially isolated product from the present process often contains varying amounts of hydrogen fluoride, which is also removed by basification. Although the crude product from the present process is usually sufficiently pure, after appropriate basification, for immediate acylation to produce an antibacterial agent, it can be purified further if desired. A simple method of purification involves dissolution in water at pH 7, re-adjustment of the pH to the isoelectric point of the product (ca. pH 4.1), followed by concentration of the aqueous solution to small volume and recovery of the purified product by filtration. From the foregoing, it will be apparent that the choice of a particular acid-addition salt, in the instance wherein the starting compound of formula I is used as an acid-addition salt, is not affected by the pharmaceutical acceptability or non-acceptability of the acid component of the acid-addition salt, since the acid component is eliminated before acylation.

The compounds of formula I, wherein $R^1$ is triphenylmethyl or the said substituted triphenylmethyl are prepared by the following four-step sequence.

In step 1, 6-aminopenicillanic acid is reacted with triphenylmethyl chloride or the appropriately-substituted triphenylmethyl chloride to produce a compound of formula II,

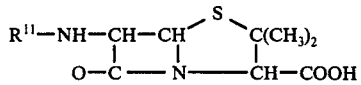

(II)

wherein $R^{11}$ is triphenylmethyl or the acid substituted triphenylmethyl. The reaction is carried out using standard methods: see, for example, Sheehan and Henery-Logan, *Journal of the American Chemical Society*, 81, 5838 (1959); Koe, *Nature*, 1200 (1962). Substituted triphenylmethyl chlorides are prepared by standard methods: see, for example, "Organic Syntheses," Collective Volume 3, John Wiley & Sons, Inc., 1955, pages 839–846.

In Step 2, the compound of formula II, wherein $R^{11}$ is triphenylmethyl or the said substituted triphenylmethyl is converted into the corresponding amide of formula III.

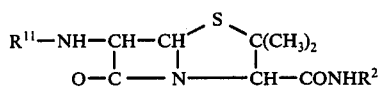

(III)

wherein $R^{11}$ is triphenylmethyl or the said substituted triphenylmethyl and $R^2$ is as previously defined. The conversion is carried out via activation of the 3-carboxy group by mixed anhydride formation, followed by reaction of the mixed anhydride with an amine of formula $R^2$-$NH_2$, wherein $R^2$ is selected from the group consisting of

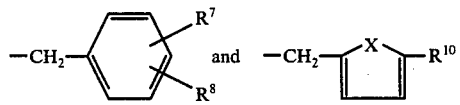

wherein $R^7$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, benzyloxy and phenyl; $R^8$ is selected from the group consisting of hydrogen, hydroxy, fluoro, chloro, unbranched-alkyl having from one to six carbon atoms and unbranched-alkoxy having from one to six carbon atoms; $R^{10}$ is selected from the group consisting of hydrogen and methyl; and X is selected from the group consisting of oxygen and sulfur; provided that at least one of $R^7$ and $R^8$ is selected from the group consisting of 2-hydroxy, 4-hydroxy, 4-alkoxy having from one to six carbon atoms, 2-(unbranched-alkoxy) having from one to six carbon atoms and 4-benzyloxy is present. This produces the necessary compounds of formula III.

The individual reactions of Step 2 are carried by standard methods. Thus, formation of the mixed anhydride involves suspending or dissolving an appropriate carboxylate salt of the compound of formula II in a reaction-inert organic solvent, and then adding to this suspension or solution pivaloyl chloride or a lower-alkyl chloroformates. Appropriate salts are, for example, alkali metal salts, such as sodium or potassium salts, and amine salts, such as triethylammonium, pyridinium, N-ethylpiperidinium or N,N-dimethylanilinium salts. Appropriate solvents are those which serve to dissolve at least one of the reactants, and the mixed anhydride product, and do not adversely interact with the reactants or product. Examples of such solvents are chlorinated hydrocarbons, such as chloroform, methylene chloride; aromatic hydrocarbons, such as benzene, toluene and xylene; and ethers, such as diethyl ether, tetrahydrofuran and 1,2-dimethoxyethane. The reaction is usually carried out at a temperature in the range from about −50° C. to about 30° C., and preferably at about 0° C. At about 0° C., the reaction commonly requires about one hour. The penicillanic acid salt and the pivaloyl chloride or lower-alkyl chloroformate are normally present in roughly equimolar proportions, although in some instances a small excess of the acid chloride component is used. The product can be isolated simply by filtering off the insoluble materials, and then evaporating the solvent in vacuo to give the crude product. The latter can be used directly, or purified further by methods known in the art. If desired, however, the mixed anhydride product need not be isolated. It can be used in situ for reaction with the amine of formula $R^2$—$NH_2$. Reaction of the mixed anhydride with the amine of formula $R^2$—$NH_2$ is usually carried out simply by contacting the reactants in an inert solvent, for about 0.5 to about 2.0 hours, at a temperature in the range from about −30° C. to about 30° C. and preferably at around 0° C. The same solvents identified above for mixed anhydride formation are useful for the instant reaction, and the reagents are usually used in approximately equimolar proportions. As will be realized by one skilled in the art, the product should not be exposed to an excess of the starting amine, since this runs the risk of causing extensive decomposition of the penam β-lactam. In the cases wherein this reaction is conducted in a water-immiscible solvent, the product is usually isolated by washing the reaction mixture with water and then concentrating the organic solvent to dryness in vacuo, to give the crude product. The latter product can be used immediately, or, if desired, it can be purified further by well-known methods. However, it is sometimes convenient simply to wash the reaction mixture with water, and then use the so-produced solution of amide directly. In the cases wherein the reaction is conducted in a water-miscible solvent, the product is usually isolated by first removing the water-miscible solvent by evaporation in vacuo, replacing it by a water-immiscible solvent, and then proceeding as described above.

In Step 3, the compound of formula III, wherein $R^{11}$ is triphenylmethyl or the said substituted triphenylmethyl and $R^2$ is as previously defined, is converted into an imidoyl chloride of formula IV.

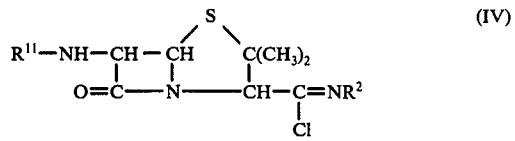

(IV)

For imidoyl chloride formation, a convenient method comprises dissolving the amide in a reaction-inert organic solvent and then treating the solution with phosgene and a tertiary amine. About one molar equivalent of phosgene is usually used, but amounts up to about two or three molar equivalents are sometimes employed. The tertiary amine is preferably present in an amount equal to or greater than the amount of phosgene. The reaction is carried out at a temperature in the range from about −20° C. to about 30° C., and preferably at about 25° C., and it usually requires a few hours to reach completion. It is sometimes advantageous, from a standpoint of hastening complete conversion to imino chloride, to add further quantities of tertiary amine and phosgene as the reaction proceeds. A variety of tertiary amines can be used in this process, for example trimethylamine, triethylamine, N,N-dimethylaniline, N-methylmorpholine and pyridine, and the like and typical solvents which can be used are chlorinated hydrocarbons, such as chloroform, methylene chloride and 1,2-dichloroethane, and ethers such as tetrahydrofuran and 1,2-dimethoxyethane. If desired, the imidoyl chloride can be isolated by evaporation of the filtered reaction mixture, but in many instances it is convenient to use the imino chloride in situ. Several other reagents, for example, thionyl chloride or a phosphorus halide such as phosphorus pentachloride are operative in the imidolyl chloride forming reaction.

In Step 4, the so-produced imidoyl chloride of formula IV is converted into the desired tetrazolylpenam compounds of formula I. This is carried out by treating the said imidoyl chloride with a source of azide ion, and a convenient way of carrying out this transformation involves dissolving the imidoyl halide in an appropriate solvent, and then adding about one molar equivalent, or sometimes a small excess, of the azide ion source. The reaction mixture is then stored at or about ambient temperatures for several hours, for example, overnight, until conversion into tetrazole is substantially complete. A wide variety of azide ion sources are operative in this process, and examples of those which are particularly valuable are trialkylsilyl azides having from one to four carbon atoms in each of said alkyl groups, such as trimethylsilyl azide and triethylsilyl azide; salts of hydrazoic acid, such as potassium azide sodium azide, tributylammonium azide, N,N-dimethylanilinium azide, N-methylmorpholinium azide and pyridinium azide; tetramethylguanidinium azide. Appropriate solvents are those which will serve to dissolve both the imidoyl halide and the azide ion source, but do not adversely react with either the reactants or the products of the process. In the cases where the azide ion source is a trialkylsilyl azide or a trisubstituted ammonium azide, chlorinated hydrocarbon solvents, such as chloroform, methylene chloride and 1,2-dichloroethane, are commonly used. However, dipolar aprotic solvents such as N-methylpyrrolidone, can also be used; and in the cases where a metal salt of hydrazoic acid constitutes the azide ion source, these dipolar aprotic solvents become the solvent-type of choice. As regards ease of operation, and availability of reagents, the use of trimethylsilyl azide in chloroform is particularly convenient. As indicated earlier, the reaction takes several hours to reach completion. However, the conversion to tetrazole can often be hastened by adding further quantities of azide ion during the course of the reaction. Product isolation is achieved using standard methods. When a low boiling chlorinated hydrocarbon is the solvent, the reaction solution is washed with dilute alkali and then the organic solvent is evaporated off. When a dipolar aprotic solvent is the solvent, the reaction mixture is usually first diluted with a large excess of dilute alkali, and then, after appropriate adjustment of the pH, the product is isolated by solvent extraction.

It should be noted that a minor variation in the last two steps of this four-step sequence is often used, in the specific instance wherein $R^2$ contains a phenolic hydroxy group. In this case, it is usually desirable to protect the hydroxy group as its trimethylsilyl ether, before imidoyl chloride formation. The trimethylsilyl group is introduced by methods well-known in the art, such as, for example, using trimethylchlorosilane, as discussed by Birkofer and Ritter in Angewandte Chemie (International Edition in English), 4, 417–418 and 426 (1965). The trimethylsilyl group can be removed, after formation of the tetrazole ring, by exposure of the product to a protic solvent system, such as water or methanol.

The starting materials of formula I, wherein $R^1$ is hydrogen and $R^2$ is as previously defined, are prepared from the corresponding compound, wherein $R^1$ is triphenylmethyl or the said substituted triphenylmethyl, by removal of the triphenylmethyl or substituted triphenylmethyl protecting group by treatment with acid. A wide variety of acidic reagents and conditions known in the art for removal of the triphenylmethyl group are operable in this process. For example, it is possible to use a sulfonic acid, such as methanesulfonic acid, benzenesulfonic acid or p-toluenesulfonic acid; an anhydrous hydrohalic acid, such as hydrogen chloride or hydrogen bromide; or an alkanoic acid, such as acetic acid, propionic acid, chloroacetic acid, trifluoroacetic acid and the like. The reaction is normally carried out by dissolving the starting material in an appropriate solvent and adding about two molar equivalents of the acid reagent, at or about ambient temperature. Reaction is complete within about one hour, and the product is present in the reaction medium in the form of the acid-addition salt corresponding to the acidic reagent used. A solvent should be chosen which will dissolve the starting penam, and examples of solvents which find use are: ethers, such as diethyl ether, tetrahydrofuran, dioxane and 1,2-dimethoxyethane; chlorinated hydrocarbons, succh as chloroform, methylene chloride and 1,2-dichloroethane; lower aliphatic ketones such as acetone, methyl ethyl ketone and methyl isobutyl ketone; esters, such as ethyl acetate and butyl acetate; hydrocarbons, such as hexane, cyclohexane and benzene; and lower alkanols, such as methanol, ethanol and butanol. Although it is common to use about two molar equivalents of acid in this process, only one molar equivalent is necessary when either the reaction is carried out in the presence of one molar equivalent of water, or the acid is introduced as a monohydrate. However, as will be realized by one skilled in the art, the product from this reaction should not be exposed to an excess of acid for prolonged periods, since in this case there is a danger of destroying the β-lactam system. A particularly convenient mode of operation for this process, is to choose an acid-solvent system such that the starting material is soluble, but the acid-addition salt generated during the reaction precipitates as it is formed. It can then be recovered by filtration at the end of the reaction. When using the combination of p-toluenesulfonic acid in acetone, the p-toluenesulfonate salt of the product often precipitates. The acid-addition salts produced by the instant process can of course be used directly as starting materials for the process of the invention. However, they can be converted to their corresponding free bases by neutralization (or basification) using conventional methods.

As indicated hereinbefore, 6-amino-2,2-dimethyl-3-(5-tetrazolyl)penam is useful as a chemical intermediate, since conversion into 6-acylamino-2,2-dimethyl-3-(5-tetrazolyl)penam compounds produces valuable antibacterial agents. For example, 6-amino-2,2-dimethyl-3-(5-tetrazolyl)penam can be converted into 6-(D-2-amino-2-[4-hydroxyphenyl]acetamido)-2,2-dimethyl-3-(5-tetrazolyl)penam by coupling with D-2-amino-2-(4-hydroxyphenyl)acetic acid. The coupling is carried out by: (1) protecting the amino group of the 2-amino-2-(4-hydroxyphenyl)acetic acid using methyl acetoacetate; (2) activating the free carboxy group of the protected amino acid via mixed anhydride formation; (3) reacting the mixed anhydride with the 6-amino-2,2-dimethyl-3-(5-tetrazolyl)penam; and (4) removing the enamine protecting group. This sequence is carried out in a manner analogous to that described by Long et al., *Journal of the Chemical Society*, London, Part C, 1920 (1971), for the coupling of D-2-amino-2-(4-hydroxyphenyl)acetic acid with 6-aminopenicillanic acid.

The 6-(D-2-amino-2-[4-hydroxyphenyl]acetamido)-2,2-dimethyl-3-(5-tetrazolyl)penam shows activity against a wide variety of gram-positive and gram-negative bacteria. The in vitro activity can be demonstrated by the conventional two-fold serial dilution technique in Brain-Heart Infusion broth (Difco). The broth is inoculated with the bacterial culture, and with the test compound, and then it is incubated overnight. On the next day, the test is read visually. The minimum inhibitory concentration (MIC) is the lowest concentration of compound which prevents turbidity, i.e., which prevents growth of the microorganism. In vitro activities against certain pathogenic bacteria area shown in Table I. This in vitro activity makes the compound of value for topical applications, for example, in the form of creams and ointments, and for the sterilization of sickroom and hospital surfaces, equipment and the like. 6-(D-2-Amino-2-[4-hydroxyphenyl]acetamido is also active as an antibacterial agent in vivo. In determining such activity, the compound is administered to infected mice, using a multiple dosing regimen. The severity of infection varies from about one to about ten times that needed to kill 100% of the mice under the conditions of the test. At the end of the test, the activity of the compound is assessed by counting the number of survivors among the treated animals. Both the subcutaneous (SC) and the oral (PO) dosage routes are used. Results are given in Table II, wherein the ability of the compound to protect mice against systemic infections caused by a lethal intraperitoneal inoculum of *Staphylococcus aureus* or of *Escherichia coli* is demonstrated. This in vivo activity makes this compound suitable for the control of bacterial infections caused by susceptible organisms, in mammals, including man, by both the oral and parenteral mode of administration.

For therapeutic use of 6-(D-2-amino-2-[4-hydroxyphenyl]acetamido)-2,-2-dimethyl-3-(5-tetrazolyl)penam or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, 6-(D-2-amino-2-[4-hydroxyphenyl]acetamido)-2,2-dimethyl-3-(5-tetrazolyl)penam can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, Table I

| In Vitro Antibacterial Activity of 6-(D-2-Amino-2-[4-hydroxyphenyl]-acetamido)-2,2-dimethyl-3-(5-tetrazolyl)penam | |
|---|---|
| Microorganism | MIC(mcg./ml.) |
| *Staphylococcus aureus* | 0.006 |
| *Streptococcus pyogenes* | 0.001 |
| *Escherichia coli* | 0.78 |

Table II

| In Vivo Antibacterial Activity of 6-(D-2-Amino-2-[4-hydroxphenyl]-acetamido)-2,2-dimethyl-3-(5-tetrazolyl)penam | | | |
|---|---|---|---|
| Dosage (mg./kg.) | Dosage route | Percentage protection | |
| | | S. Aureus | E. coli |
| 50 | SC | 80 | 100 |
| 25 | SC | 70 | 80 |
| 12 | SC | 50 | |
| 6 | SC | 50 | |
| 200 | PO | | 100 | sterile solutions of the active ingredient are usually prepared, and the pH of the solutions are suitably adjusted and buffered. For intravenous use, the total concentration of solutes should be controlled to render the preparation isotonic.

When 6-(D-2-amino-2-[4-hydroxyphenyl]acetamido)-2,2-dimethyl-3-(5-tetrazolyl)penam is used in human subjects, the prescribing physician will ultimately determine an appropriate dosage for a given patient. This dosage will be expected to vary according to the age, weight and response of the individual patient, as well as the nature and severity of the patient's symptoms. However, the compound will normally be used both orally and parenterally at a dosage in the range from about 1 g to about 5 g per day, in divided doses.

The following examples are provided for further illustration of the invention.

EXAMPLE I

Reaction of 6-(Triphenylmethylamino)-2,2-dimethyl-3-(1-[4-methoxybenzyl]tetrazol-5-yl)penam with Hydrogen Fluoride To 4 ml. of hydrogen fluoride, covered with a layer of hexane, at ca. −80° C., is added 2.4 g. of 6-(triphenylmethylamino)-2,2-dimethyl-3-(1-[4-methoxybenzyl]tetrazol-5-yl)penam. The reaction vessel is then transferred to an ice-water bath, and the reaction mixture is held at ca. 0° C. for 1.5 hours. At this point, the hexane is removed by decantation, and the hydrogen fluoride solution is poured with stirring into 60 ml. of diisopropyl ether which has been pre-cooled to −40° C. Stirring is continued for a further 10 minutes, and the solid which has precipitated is removed by filtration to give 1.46 g. of crude product.

The above crude product is stirred with 30 ml. of water, at 0°–5° C., and at pH 8.0 for 20 minutes, and then the mixture is filtered. The aqueous filtrate is washed with chloroform, and then the pH is lowered to 4.0. This latter solution is concentrated to small volume in vacuo. The precipitate which forms is filtered off, giving 416 mg. (43% yield) of 6-amino-2,2-dimethyl-3-(5-tetrazolyl)penam. The NMR spectrum of the product shows absorptions at 6.65 ppm (broad singlet, 3H), 5.64 ppm (doublet, 1H) 5.20 ppm (singlet, 1H), 4.65 ppm (doublet, 1H), 1.60 ppm (singlet, 3H) and 1.03 ppm (singlet, 3H). By hydroxylamine assay, the compound is 97.4% pure.

EXAMPLE II

Reaction of each of the 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam compounds, listed in Tables III and IV below, with hydrogen fluoride, according to the procedure of Example I, produces, in each case, 6-amino-2,2-dimethyl-3-(5-tetrazolyl)penam.

TABLE IV

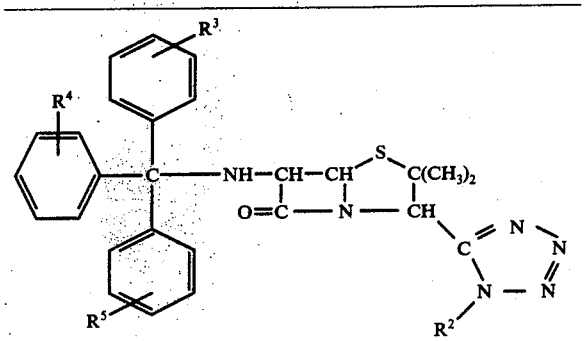

| $R^2$ | $R^3$ | $R^4$ | $R^5$ |
|---|---|---|---|
| furfuryl | 3-$CH_3CH_2O$ | H | H |
| furfuryl | 2-F | H | H |
| furfuryl | 3-$CH_3$ | H | H |
| furfuryl | 3-$CH_3O$ | 3-$CH_3O$ | 3-$CH_3O$ |
| 5-methylfurfuryl | 4-$CH_3$ | H | H |
| 5-methylfurfuryl | 3-$CH_3CH_2$ | 3-$CH_3CH_2$ | H |
| (2-thienyl)methyl | H | H | H |
| (2-thienyl)methyl | 4-$C_6H_5$ | H | H |
| (5-methyl-2-thienyl)methyl | H | H | H |
| furfuryl | H | H | H |

TABLE III

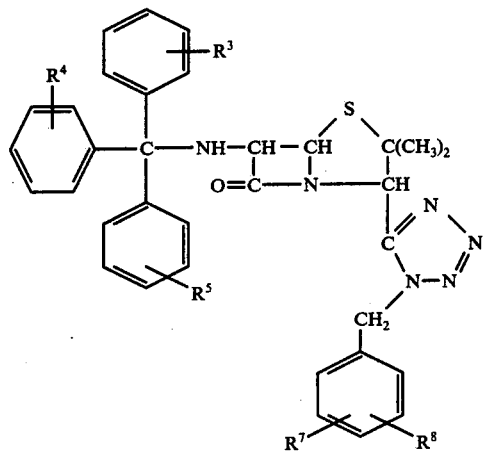

| $R^3$ | $R^4$ | $R^5$ | $R^7$ | $R^8$ |
|---|---|---|---|---|
| H | H | H | H | 4-HO |
| H | H | H | H | 2-HO |
| H | H | H | 3-Cl | 4-HO |
| H | H | H | 3-$CH_3$ | 4-HO |
| H | H | H | 4-$CH_3CH_2O$ | 3-HO |
| H | H | H | H | 4-HO |
| H | H | H | H | 4-HO |
| Cl | H | H | 3-HO | 4-HO |
| $CH_3$ | $CH_3$ | $CH_3$ | H | 4-HO |
| $CH_3CH_2O$ | H | H | H | 4-HO |
| H | H | H | 4-$CH_3CH_2O$ | H |
| H | H | H | 4-$(CH_3)_2CHO$ | H |
| H | H | H | 4-$CH_3(CH_2)_4CH_2O$ | H |
| H | H | H | 3-Br | 4-$CH_3O$ |
| H | H | H | 3-$C_6H_5$ | 4-$CH_3O$ |
| H | H | H | 4-$CH_3O$ | H |
| H | H | H | 4-$C_6H_5$ | H |
| H | H | H | 4-$(CH_3)_2CH$ | H |
| H | H | H | 3-Cl | 4-$CH_3O$ |
| H | H | H | H | H |
| H | H | H | 3-$CH_3O$ | H |
| 4-Cl | H | H | 4-$CH_3O$ | H |
| 2-F | H | H | 3-$CH_3$ | 4-$CH_3$ |
| 3-Br | H | H | 4-$CH_3(CH_2)_4CH_2$ | H |
| 3-$CH_3O$ | H | H | 3-$CH_3O$ | 4-$CH_3O$ |
| 3-$CH_3(CH_2)_3O$ | 3-$CH_3(CH_2)_3O$ | H | 3-F | H |
| 3-$CH_3$ | 3-$CH_3$ | 3-$CH_3$ | 4-Cl | 3-Cl |
| 3-Cl | 3-Cl | 3-Cl | 4-$CH_3O$ | H |

TABLE IV-continued

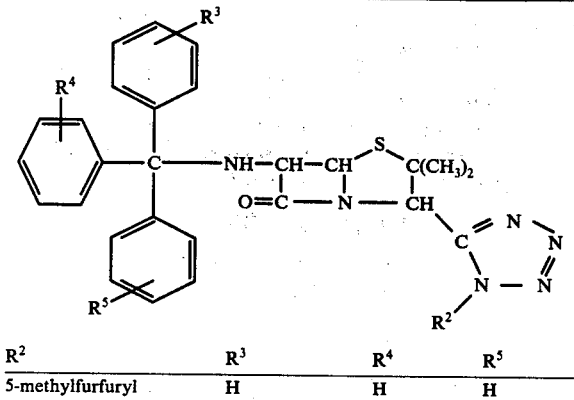

| R² | R³ | R⁴ | R⁵ |
|---|---|---|---|
| 5-methylfurfuryl | H | H | H |

EXAMPLE III

Reaction of
6-(Triphenylmethylamino)-2,2-dimethyl-3-(1-[4-methoxybenzyl]tetrazol-5-yl)penam with
p-toluenesulfonic acid and hydrogen fluoride Hydrogen fluoride gas is passed into a flask cooled in an ice-salt bath, and containing 602 mg. (0.001 mole) of 6-(triphenylmethylamino)-2,2-dimethyl-3-(1-[4-methoxybenzyl]tetrazol-5-yl)penam and 190 mg. (0.001 mole) of p-toluenesulfonic acid monohydrate, until ca. 2 ml. of liquid has condensed. The resultant solution is stored at ice-salt temperature for 1 hour, and then it is removed from the cooling bath. The bulk of the hydrogen fluoride is removed by purging the reaction flask with a stream of nitrogen, and then the residue is triturated with ca. 25 ml. of ether. The solid is filtered off, giving 487 mg. of crude 6-amino-2,2-dimethyl-3-(5-tetrazolyl)penam as its p-toluenesulfonate salt. The NMR spectrum of the product indicates that it is approximately 80% pure.

EXAMPLE IV

Reaction of
6-(Triphenylmethylamino)-2,2-dimethyl-3-(1-[4-methoxybenzyl)tetrazol-5-yl)penam with Hydrogen Fluoride Containing Anisole To 5 ml. of hydrogen fluoride, covered with a layer of hexane, and cooled to ca. −75° C., is added 1.08 g. (10 mmole) of anisole, followed by 3.01 g. (5 mmole) of 6-(triphenylmethylamino)-2,2-dimethyl-3-(1-[4-methoxybenzyl]-tetrazol-5-yl)penam. The reaction vessel is then transferred to an ice-water cooling bath, and the reaction mixture is maintained at ca 5° C. for 2.5 hours. The hexane is removed by decantation, and the hydrogen fluoride solution is poured slowly, with stirring into 50 ml. of diisopropyl ether, which has been pre-cooled to −50° C. The solid which precipitates is filtered off, giving 1.406 g. of 6-amino-2,2-dimethyl-3-(5-tetrazolyl)penam.

The above crude product is added to a mixture of 20 ml. of water and 10 ml. of ethyl acetate. The pH is adjusted to 7.8 and the ethyl acetate is removed and discarded. The pH of the aqueous phase is then adjusted to 4.1, and the solution is concentrated to small volume in vacuo at 30° C. The solid which precipitates is recovered. This affords 541 mg. (45% yield) of 6-amino-2,2-dimethyl-3-(5-tetrazolyl)penam. By hydroxylamine assay, it is estimated to be 99% pure.

EXAMPLE V

Reaction of
6-Amino-2,2-dimethyl-3-(1-[4-methoxybenzyl)tetrazol-5-yl)penam p-Toluenesulfonate with Hydrogen Fluoride Hydrogen fluoride gas is passed into a flask cooled in an ice-salt bath, and containing 0.50 g. of 6-amino-2,2-dimethyl-3-(1-[4-methoxybenzyl]-tetrazol-5-yl)penam p-toluenesulfonate, until ca. 2.0 ml. of liquid has condensed. The solution thus obtained is stored in the ice-salt bath for a further 1 hour, and then it is removed from the cooling bath. The solvent is removed by purging the reaction system with nitrogen gas, and then the residue is triturated for 1 hour under diethyl ether. Finally the residue is filtered off, giving 0.33 g. (85% yield) of 6-amino-2,2-dimethyl-3-(5-tetrazolyl)penam p-toluenesulfonate. The infrared spectrum (KBr disc) of the product shows an absorption band at 1795 cm$^{-1}$ ($\beta$-lactam). The NMR spectrum shows absorption bands at 7.40 ppm (quartet, aromatic hydrogens), 5.80 ppm (doublet, C-5 hydrogen), 5.45 ppm (singlet, C-3 hydrogen), 5.20 ppm (multiplet, C-6 hydrogen), 2.25 ppm (singlet, aromatic methyl hydrogens), 1.70 ppm (singlet, C-2 methyl hydrogens) and 1.10 ppm (singlet, C-2 methyl hydrogens).

EXAMPLE VI

Reaction of
6-Amino-2,2-dimethyl-3-(1-[4-methoxybenzyl]tetrazol-5-yl)penam p-Toluenesulfonate with Hydrogen Fluoride 1.6 Liters of hydrogen fluoride is cooled to −10° C., and then 750 g. of 6-amino-2,2-dimethyl-3-(1-[4-methoxybenzyl]tetrazol-5-yl)penam p-toluenesulfonate is added portionwise, with stirring, during 13 minutes. During the addition, the temperature rises to 1° C. After the addition is complete, the reaction medium is maintained at ca. 0° C., with stirring, for 2 hours and then the hydrogen fluoride solution is added dropwise, with stirring to 36 liters of diisopropyl ether which has been previously cooled to 0° C. During this latter addition, the temperature rises to ca. 28° C., and a precipitate forms. This mixture is stirred at ambient temperature for 0.5 hour, and then the precipitate is filtered off. It is washed with a further quantity of diisopropyl ether, and then dried, affording 550 g. (95% yield) of 6-amino-2,2-dimethyl-3-(5-tetrazolyl)penam p-toluenesulfonate.

EXAMPLE VII

Reaction of each of the 6-amino-2,2-dimethyl-3-(1-substituted tetrazol-5-yl)penam p-toluenesulfonate compounds listed in Table V below, with hydrogen fluoride, according to the procedure of Example VI, produces in each case 6-amino-2,2-dimethyl-3-(5-tetrazolyl)penam p-toluenesulfonate.

TABLE V p-CH$_3$—C$_6$H$_4$SO$_3$—

TABLE V-continued

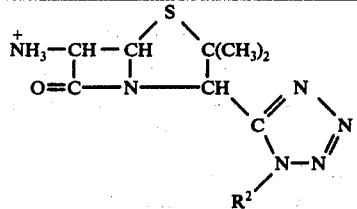

R²

4-hydroxybenzyl
2-hydroxybenzyl
3-chloro-4-hydroxybenzyl
4-hydroxy-3-methylbenzyl
3,4-dihydroxybenzyl
5-methylfurfuryl
2,4-dimethoxybenzyl
2-methoxybenzyl
4-ethoxybenzyl
4-isopropoxybenzyl
4-n-hexyloxybenzyl
4-benzyloxy-3-chlorobenzyl
4-ethoxy-2-fluorobenzyl

R²

3-bromo-4-methoxybenzyl
4-iodo-2-methoxybenzyl
4-isobutoxy-3-methylbenzyl
3,4-di(n-propoxy)benzyl
3-phenyl-4-methoxybenzyl
3,4-dimethylbenzyl
4-n-hexylbenzyl
4-ethoxy-3-phenylbenzyl
5-methylfurfuryl
(2-thienyl)methyl
(5-methyl-2-thienyl)methyl
4-benzyloxybenzyl
furfuryl

EXAMPLE VIII

Reaction of
6-Amino-2,2-dimethyl-3-(1-[4-methoxybenzyl]-tetrazol-5-yl)penam p-toluenesulfonate with Hydrogen Fluoride Containing Anisole To a mixture of 36 kg of hydrogen fluoride and 34.7 liters of anisole, cooled to −15° C., is added 16.266 kg. of 6-amino-2,2-dimethyl-3-(1-[4-methoxybenzyl]tetrazol-5-yl)penam p-foluenesulfonate. The reaction mixture is maintained at −2° C. to 2° C. for 3 hours, and then it is poured into 790 liters of diisopropyl ether, which has been precooled to −15° C. The precipitate is recovered by filtration, washed with more diisopropyl ether, and dried, giving 12.850 kg. (93% yield) of 6-amino-2,2-dimethyl-3-(5-tetrazolyl)penam p-toluenesulfonate salt. By hydroxylamine assay the product is 74.8% pure.

EXAMPLE IX

Reaction of
6-Amino-2,2-dimethyl-3-(1-[4-methoxybenzyl]tetrazol-5-yl)penam p-Toluenesulfonate with Hydrogen Fluoride Containing Acetic Acid Hydrogen fluoride gas is passed into a polyethylene flask, cooled to −10° C., until 3 ml. has condensed. To the hydrogen fluoride is then added 0.45 ml. of glacial acetic acid, and the mixture is cooled to −20° C. To the mixture is added 1.065 g. of 6-amino-2,2-dimethyl-3-(1-[4-methoxybenzyl]tetrazol-5-yl)penam p-toluenesulfonate over a 3 minute period. The reaction mixture is stirred at 0° C. for 2 hours, and then it is poured, with stirring, into an excess of ether, pre-cooled to −40° C. After 30 minutes, the precipitate is filtered off, giving 0.681 g. of crude 6-amino-2,2-dimethyl-3-(5-tetrazolyl)-penam p-toluenesulfonate, which is ca 60% pure.

PREPARATION A 6-(Triphenylmethylamino)-2,2-dimethyl-3-(1-[4-methoxybenzyl]-tetrazol-5-yl)penam (A). 6-(Triphenylmethylamino)-2,2-dimethyl-3-(N-[4-methoxybenzyl]carbamoyl)-penam.

To a stirred slurry of 86.4 g. (0.4 mole) of 6-aminopenicillanic acid in 600 ml. of anhydrous chloroform is added 111.2 ml. (0.8 mole) of triethylamine, and the mixture is stirred at ambient temperature until a clear solution is obtained (ca. 15 minutes). To this solution is then added, portionwise over about 25 minutes, 134.9 g. (0.44 mole) of 90% pure triphenylmethyl chloride, at ambient temperature. Stirring is continued for a further 64 hours, and then 5.6 ml. of triethylamine is added. The solution is cooled to 0°-5° C., and then an ice-cold solution of 38 ml. (0.4 mole) of ethyl chloroformate in 80 ml. of chloroform is added dropwise during 30 minutes with the reaction temperature being maintained between 4 and 9° C. After a further 15 minutes of stirring, 52.4 ml. (0.4 mole) of 4-methoxybenzylamine is injected into the reaction medium, below the surface of the solvent, at 4° to 9° C., and over a period of 30 minutes. Stirring is continued for a further 30 minutes at 3° to 6° C., for 20 minutes while the reaction medium warms to 20° C. The reaction mixture is then washed with water, followed by brine. Finally, it is dried using magnesium sulfate to give a chloroform solution of 6-(triphenylmethylamino)-2,2-dimethyl-3-(N-[4-methoxybenzyl]carbamoyl)penam.

(B). 6-(Triphenylmethylamino)-2,2-dimethyl-3-(1-[4-methoxybenzyl]tetrazol-5-yl)penam.

To a chloroform solution containing 69.4 g. (0.120 mole) of 6-(triphenylmethylamino)-2,2-dimethyl-3-(N-[4-methoxybenzyl]carbamoyl) penam, and having a volume of 133.3 ml., prepared by the method described in (A) above, is added a further 132.7 ml. of chloroform, followed by 29.1 ml. (0.360 mole) of pyridine. This solution is cooled to 10° C., and then 26.22 g. (0.126 mole) of phosphorus pentachloride is added during 15 minutes, with stirring. Stirring is continued at ca. 10° C. for 10 minutes, and then at ambient temperature for a further 1.5 hours, giving a solution of the imino chloride. To a one-sixth aliquot of this imino chloride solution is added 4.85 ml. (0.060 mole) of pyridine, followed by 2.42 ml. (0.060 mole) of methanol at ca. 25° C., with stirring. After a further 15 minutes of stirring 2.03 g. (0.038 mole) of ammonium chloride, followed by 2.59 g. (0.038 mole) of 95% pure sodium azide, is added. The reaction mixture is then stirred at ambient temperature for a further 4 hours. At this point, 400 ml. of water and 200 ml. of chloroform are added, and then the layers are separated. The organic phase is washed with water, dried using magnesium sulfate, and then concentrated to a small volume in vacuo. This final chloroform solution is added dropwise with stirring to a large volume of diisopropylether, and, after 30 minutes, the precipitate which has formed is filtered off. This affords 6.1 g. of 6-(triphenylmethylamino)-2,2-dimethyl-3-(1-[4-methoxybenzyl]-tetrazol-5-yl)penam. The infrared spectrum of the product (KBr disc) shows an absorption band at 1790 cm$^{-1}$ ($\beta$-lactam); and the NMR spectrum (in CDCl$_3$) shows absorptions at 7.25 ppm (multiplet, aromatic hydrogens), 5.40 ppm (broad singlet, benzyl hydrogens), 5.05 ppm (singlet, C-3-hydrogen), 4.50–4.30 ppm (multiplet, C-5and C-6hydrogens), 3.70 ppm (singlet, methoxy hydrogens), 3.50–3.10 ppm (broad peak, NH), 1.50 ppm (singlet, C-2-methyl hydrogens) and 0.75 ppm (singlet, C-2-methyl hydrogens).

PREPARATION B 6-(Triphenylmethylamino)-2,2-dimethyl-3-(1-[4-benzyloxybenzyl]-tetrazol-5-yl)penam 6-(Triphenylmethlamino)-2,2-dimethyl-3-(N-[4-benzyloxybenzyl]carbamoyl)-penam.

To a stirred solution of 20.0 g. of 6-triphenylmethylaminopenicillanic acid (Sheehan and Henery-Logan, *Journal of the American Chemical Society*, 81, 5838 [1959]) in 140 ml. of acetone, at 0°–5° C., is added 6.08 ml. of triethylamine followed by 5.78 ml. of isobutyl chloroformate. After a further 10 minutes, the mixture is filtered directly into a stirred solution of 9.28 g. of 4-benzyloxybenzylamine in 1,000 ml. of water and 300 ml. of acetone at ambient temperature. The mixture so obtained is stirred for 4 minutes, and then an additional 500 ml. of water is added. Stirring is continued for a further 7 minutes, and then the reaction mixture is extracted with ether. The ether is dried using anhydrous magnesium sulfate, and then evaporated to dryness in vacuo. The crude product so obtained is re-dissolved in 200 ml. of ether, which is then added dropwise over 10 minutes to 2,500 ml. of hexane. The solid which precipitates is filtered off, giving 21.5 g. of 6-(triphenylmethylamino)-2,2-dimethyl-3-(N-[4-benzyloxybenzyl]carbamoyl)penam.

6-(Triphenylmethylamino)-2,2-dimethyl-3-(1-[4-benzyloxybenzyl]-tetrazol-5-yl)-penam.

To a stirred solution of 2.0 g. of the above-described amide in 10 ml. of dry chloroform, at 0°–5° C., is added 0.99 ml. of pyridine, followed by 5.42 ml. of a 2.26 M solution of phosgene in chloroform. The reaction mixture is then stirred at ambient temperature overnight. At this point, it is evaporated to dryness in vacuo, yielding a viscous gum, which is extracted with 100 ml. of ether. The ether is filtered, and evaporation of the filtrate affords the imino chloride as a yellow foam. The imino chloride is then redissolved in 8 ml. of dry N,N-dimethylformamide. To this solution is added 249 mg. of potassium azide, and the turbide solution is stirred at ambient temperature for 2.25 hours. The solvent is evaporated at ambient temperature, under high vacuum, leaving a brown gum. This residue is partitioned between 60 ml. of water and 150 ml. of ether. The ether phase is separated off, washed with saturated brine, dried using anhydrous sodium sulfate, and finally evaporated to dryness in vacuo. The residue is 980 mg. of 6-(triphenylmethylamino)-2,2-dimethyl-3-(1-[4-benzyloxybenzyl]tetrazol-5-yl)penam. Its NMR spectrum (in CDCl$_3$) shows absorption bands at 7.30 ppm (multiplet, aromatic hydrogens), 5.45 ppm (quartet, benzyl hydrogens), 5.05 ppm (singlet, C-3 hydrogen), 5.00 ppm (singlet, benzyl hydrogens), 4.40 ppm (multiplet, C-5 and C-6-hydrogens), 1.40 ppm (singlet, C-2-hydrogen), and 0.70 ppm (singlet, C-2 hydrogen).

PREPARATION C 6-(Triphenylmethylamino)-2,2-dimethyl-3-(1-[4-hydroxybenzyl]-tetrazol-5-yl)penam (A) 6-Triphenylmethylamino)-2,2-dimethyl-3-(N-[4-hydroxybenzyl]carbamoyl)-penam.

To a stirred slurry of 43.2 g. (0.20 mole) of 6-aminopenicillanic acid in 300 ml. of chloroform is added 55.6 ml. (0.40 mole) of triethylamine, followed by 61.2 g. (0.22 mole) of triphenylmethyl chloride, at ambient temperature. Stirring is then continued for a further 48 hours at ambient temperature.

A 120-ml. portion (containing 0.060 mole of triethylammonium 6-[triphenylmethylamino]penicillanate) of the above chloroform solution is withdrawn. It is diluted with a further 40 ml. of chloroform, and then 1.67 ml. (0.012 mole) of triethylamine is added. The mixture is cooled to ca. 4° C., in an ice-bath, and then 6.84 ml. of ethyl chloroformate is added all at once, with stirring. Stirring is continued for 30 minutes with ice-bath cooling, and then 7.5 g. (0.060 mole) of 4-hydroxybenzylamine is added. Stirring is continued for 10 minutes with ice-bath cooling, and then for a further 1 hour without cooling. At this point, the chloroform solution is washed with water, followed by brine, and then dried using anhydrous sodium sulfate. Removal of the solvent by evaporation in vacuo affords the crude amide. The crude amide is re-dissolved in 50 ml. of chloroform and absorbed on a column of chromatographic grade silica gel. The column is eluted with chloroform, taking 400 ml. fractions. Fractions 9 to 15 are combined and concentrated to an oil, which solidifies on trituration with methylene chloride. After further trituration with ether, there is obtained 12.63 g. of 6-(triphenylmethylamino)-2,2-dimethyl-3-(N-[4-hydroxybenzyl]carbamoyl)penam, m.p. 166°–168° C. (dec.). The infrared spectrum of the product (CHCl$_3$ solution ) shows absorptions at 1785 cm$^{-1}$ ($\beta$-lactam) and 1675 cm$^{-1}$ (amide I). The NMR spectrum of the product (CDCl$_3$) shows absorptions at 7.60–6.40 ppm (multiplet, 20H, aromatic hydrogens and amide hydrogen), 4.70–4.10 ppm (multiplet, 5H, G-5 and C-6 hydrogens, benzyl methylene hydrogens and C-3hydrogen), 2.98 ppm (doublet, 1H, amine nitrogen), 1.64 ppm (singlet, 3H, C-2-methyl hydrogens) and 1.31 ppm (singlet, 3H, C-2 methyl hydrogens).

(B) 6-(Triphenylmethylamino)-2,2-dimethyl-3-(1-[4-hydroxybenzyl]tetrazol-5-yl)penam.

To a stirred solution of 1.69 g. (3 m mole) of 6-(triphenylmethylamino)-2,2-dimethyl-3-(N-[4-hydroxybenzyl]carbamoyl)penam (prepared as described in A) in 9 ml. of chloroform is added 1 ml. (12 m mole) of pyridine. The solution is cooled to ca. 4° C. in an ice-bath and 0.80 ml. of chlorotrimethylsilane is added. The solution is stirred for 40 minutes at ambient temperature, and then it is again cooled to ca. 4° C. Phosgene (1.5 ml. of a 4.3 M solution in chloroform (6.45 m mole) is added and the cooling bath is removed. Stirring is continued for a further 1.5 hours, and then all the volatile components are removed by evaporation in vacuo.

The oily residue is redissolved in 6 ml. of chloroform and the solution is cooled to ca. 4° C. in an ice-bath. To the stirred solution is added 0.95 g. (6 m mole) of tetramethylguanidinium azide, and then stirring is continued for a further 1 hour at ambient temperature. At this point, 25 ml. of water is added, followed by sufficient 1 N sodium hydroxide to bring the pH of the aqueous phase to 10. The chloroform layer is separated off, washed with water, dried using sodium sulfate, and evaporated to dryness in vacuo. The oily residue (2.3 g.) is dissolved in a small volume of chloroform and absorbed on a column of 30 g. of chromatographic silica gel. The column is eluted with chloroform, taking 50-ml. fractions. Fractions 13 to 19 are combined and concentrated in vacuo to give 0.71 of 6-(triphenylmethylamino)-2,2-dimethyl-3-(1-[4-hydroxybenzyl]tetrazol-5-yl)penam. The infrared spectrum of the product (in CHCl$_3$) shows an absorption at 1780 cm$^{-1}$ ($\beta$-lactam). The NMR spectrum (CDCl$_3$) shows absorptions at 7.80–6.67 ppm (multiplet, 20H, aromatic hydrogens and phenolic hydrogen), 5.66–5.10 ppm (quartet, 2H, benzyl methylene hydrogens), 5.02 ppm (singlet, 1H, C-3 hyrogen), 4.60–4.20 ppm (multiplet, 2H, C-5 and C-6 hydrogen), 3.10 ppm (doublet, 1H, amine hydrogen), 1.44 ppm (singlet, 3H, C-2 methyl hydrogens) and 0.71 ppm (singlet, 3H, C-2 methyl hydrogens).

PREPARATION D

The procedure of Preparation C is repeated, except that where necessary the triphenylmethyl chloride is replaced by the appropriately-substituted triphenylmethyl chloride, and where necessary the 4-hydroxybenzylamine is replaced by the requisite primary amine. This affords the following compounds:

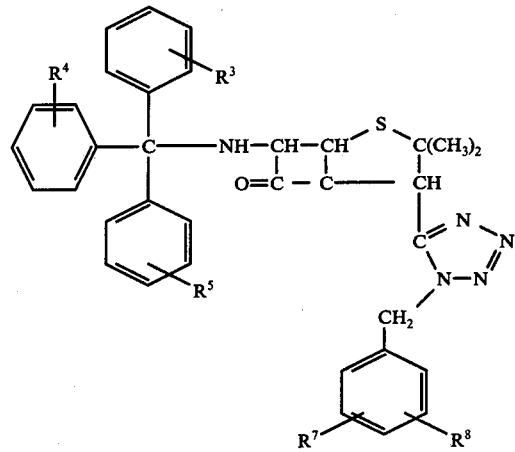

| R$^3$ | R$^4$ | R$^5$ | R$^7$ | R$^8$ |
|---|---|---|---|---|
| H | H | H | H | 2-OH |
| H | H | H | 3-Cl | 4-OH |
| H | H | H | 3-CH$_3$ | 4-OH |
| H | H | H | 4-OCH$_2$CH$_3$ | 3-OH |
| H | H | H | H | 4-OH |
| H | H | H | H | 4-OH |
| Cl | H | H | 3-OH | 4OH* |
| CH$_3$ | CH$_3$ | CH$_3$ | H | 4-OH |
| CH$_3$CH$_2$O | H | H | H | 4-OH |

*In this case, it is necessary to double the molar proportions of the pyridine and chlorotrimethylsilane used for protection of the phenol hydroxy groups prior to imino chloride formation.

PREPARATION E 6-(Triphenylmethylamino)-2,2-dimethyl-3-(1-furfuryl-tetrazol-5-yl) penam To a stirred solution of 3.05 g. (5.7 mmole) of 6-triphenylmethylamino)-2,2-dimethyl-3-(N-furfurylcarbamoyl) penam, in 8 ml. of chloroform, at 0° C., is added 1.35 ml. (17 mmole) of pyridine, followed by 2.64 ml. of a 4.33 M solution of phosgene in chloroform. Stirring is then continued for 1 hour at 25° C. The chloroform, and excess phosgene and pyridine, are then removed by evaporation in vacuo, and the residue is redissolved in 5 ml. of chloroform. The solution is cooled to 0° C., and then 2.25 g. (14.4 mmole) of tetramethylguanidinium azide is added in several small portions. Stirring is continued for 15 minutes at ambient temperature, and then 20 ml. of chloroform, followed by 30 ml. of water, are added and the pH is adjusted to 6.5. The chloroform layer is separated off, washed with water, followed by brine, and then dried (MgSO$_4$). Removal of the solvent by evaporation in vacuo leaves 3.37 g. of a dark-red foam. The foam is re-dissolved in a small volume of chloroform and absorbed onto a column of chromatographic silica gel. Elution of the column with the same solvent, followed by evaporation of the appropriate fractions in vacuo, affords 6-(triphenylmethylamino)-2,2-dimethyl-3-(1-furfuryltetrazol-5-yl) penam. The NMR spectrum of the product (CDCl$_3$) shows absorptions at 7.40 ppm (m,16H), 6.40 ppm (m,2H), 5.50 ppm (s,2H), 5.20 ppm (s,1H), 4.90 ppm (m,2H), 1.60 ppm (s,3H), and 0.80 ppm (s,3H).

The 6-(triphenylmethylamino)-2,2-dimethyl-3-(N-furfurylcarbamoyl) penam used in this Preparation is prepared using the procedure of Preparation c (Part A), but employing furfurylamine in place of the 4-hydroxybenzylamine.

PREPARATION F 6-(Triphenylmethylamino)-2,2-dimethyl-3-(1-[5-methyl-furfuryl]tetrazol-5-yl)penam The title compound is prepared according to the procedure of Preparation E, but using 5-methylfurfurylamine in place of furfurylamine. The NMR spectrum (CDCl$_3$) of the product shows absorptions at 7.36 ppm (m, 15H), 6.33 ppm (m, 1H), 5.93 ppm (m, 1H), 5.50 ppm (s, 2H), 5.20 ppm (s, 1H), 4.50 ppm (m, 2H), 3.23 ppm (d, 1H), 2.26 ppm (s, 3H), 1.63 ppm (s, 3H) and 0.90 ppm (m, 3H).

PREPARATION G 6-(Triphenylmethylamino)-2,2-dimethyl-3-(1-[2,4-dimethoxybenzyl]-tetrazol -5-yl)penam The title compound is prepared in 46% overall yield from 6-(triphenylmethylamino) penicillanic, by replacing the furfurylamine of Preparation E by 2,4-dimethoxybenzylamine. The crude product is purified by recrystallization from a mixture of methylene chloride and methanol. The NMR spectrum of the product (CDCl$_3$) shows absorptions at 7.40 ppm (m, 16H), 6.45 ppm (m, 2H), 5.40 ppm (s, 2H), 4.50 ppm (m, 2H), 3.75 ppm (s, 3H), 3.70 ppm (s, 3H), 1.55 ppm (s, 3H) and 0.90 (s, 3H).

PREPARATION H

Starting with the appropriate 6-(triphenylmethylamino)-2,2-dimethyl-3-(N-substituted carbamoyl) penam or 6-(substituted triphenylmethylamino)-2,2-dimethyl-3-(N-substituted carbamoyl)penam, and using the procedure of Preparation E, the following congeners are prepared.

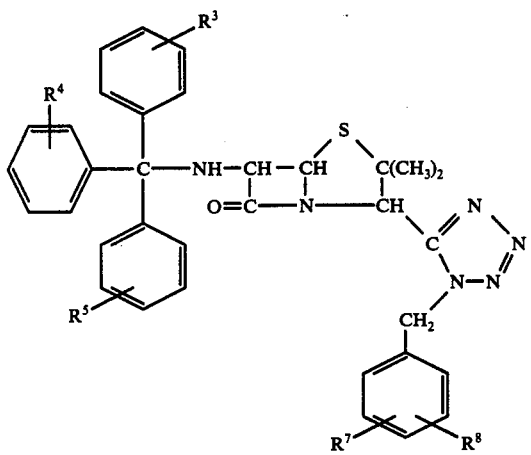

| R³ | R⁴ | R⁵ | R⁷ | R⁸ |
|---|---|---|---|---|
| H | H | H | 4-CH₃CH₂O | H |
| H | H | H | 4-(CH₃)₂CHO | H |
| H | H | H | 4-CH₃(CH₂)₄CH₂O | H |
| H | H | H | 3-Br | 4-CH₃O |
| H | H | H | 3-CH₃CH₂CH₂O | 4-CH₃CH₂CH₂O |
| H | H | H | 3-C₆H₅ | 4-CH₃O |
| H | H | H | 4-CH₃O | H |
| H | H | H | 4-C₆H₅ | H |
| H | H | H | 4-(CH₃)₂CH | H |
| H | H | H | 3-Cl | 4-CH₃O |
| H | H | H | H | H |
| H | H | H | H | H |
| H | H | H | 3-CH₃O | H |
| 4-Cl | H | H | 4-CH₃O | H |
| 2-F | H | H | 3-CH₃ | 4-CH₃ |
| 3-Br | H | H | 4-CH₃(CH₂)₄CH₂ | H |
| 3-CH₃O | H | H | 3-CH₃O | 4-CH₃O |
| 3-CH₃(CH₂)₃O | 3-CH₃(CH₂)₃O | H | 3-F | H |
| 3-CH₃ | 3-CH₃ | 3-CH₃ | 4-Cl | 3-Cl |
| 3-Cl | 3-Cl | 3-Cl | 4-CH₃O | H |

In like manner, starting with the appropriate 6-(triphenylmethylamino)-2,2-dimethyl-3-(N-substituted carbamoyl)penam or 6-(substituted triphenylmethylamino)-2,2-dimethyl-3-(N-substituted carbamoyl)penam, and employing the procedure of Preparation E, the following compounds are prepared

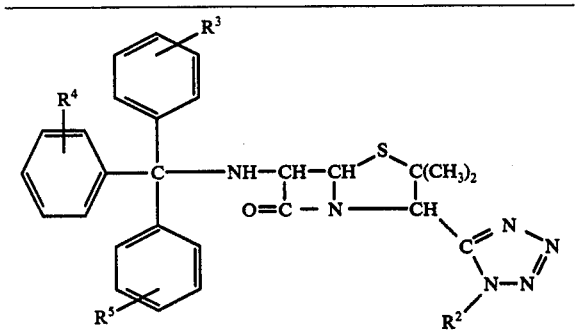

| R² | R³ | R⁴ | R⁵ |
|---|---|---|---|
| furfuryl | 3-CH₃CH₂O | H | H |
| furfuryl | 2-F | H | H |
| furfuryl | 3-CH₃ | H | H |
| furfuryl | 3-CH₃O | 3-CH₃O | 3-CH₃O |
| 5-methylfurfuryl | 4-CH₃ | H | H |
| 5-methylfurfuryl | 3-CH₃CH₂ | 3-CH₃CH₂ | H |
| (2-thienyl)methyl | H | H | H |
| (2-thienyl)methyl | 4-C₆H₅ | H | H |
| (5-methyl-2-thienyl)methyl | H | H | H |

The starting 6-(triphenylmethylamino)-2,2-dimethyl-3-(N-substituted carbamoyl)penam and 6-(substituted triphenylmethylamino)-2,2-dimethyl-3-(N-substituted carbomoyl)penam compounds, used in this Preparation, are prepared according to the procedure of Preparation C (Part A) by replacing the 4-hydroxybenzylamine used therein by an equimolar amount of the appropriate amine, and, where necessary, replacing the triphenylmethyl chloride by the appropriately substituted triphenylmethyl chloride.

PREPARATION I

6-Amino-2,2-dimethyl-3-(1-[4-methoxybenzyl]tetrazol-5-yl)penam p-toluenesulfonate To a stirred slurry of 143 g. of 6-(triphenylmethylamino)-2,2-dimethyl-3-(1-[4-methoxybenzyl]tetrazol-5-yl)penam in 1,000 ml. of dry acetone is added 45.0 g. of p-toluenesulfonic acid monohydrate, at ambient temperature. The solids slowly dissolve, giving a clear solution. After about 15 minutes, the product starts to precipitate. Stirring is continued for a further 45 minutes after the product starts to appear, and then a first crop of product is filtered off and washed with chloroform. The acetone is evaporated to dryness, and the solid residue is slurried for 45 minutes in 300 ml. of chloroform. This affords a second crop of product. The two crops are combined, slurried for 1 hour in 1,000 ml. of chloroform, filtered off, and dried in vacuo giving 123 g. of 6-amino-2,2-dimethyl-3-(1-[4-methoxybenzyl]-tetrazol-5-yl)penam p-toluenesulfonate, m.p. 174°–175° C. The infrared spectrum (KBr disc) of the product shows an absorption band at 1795 cm$^{-1}$. The NMR spectrum (in DMSO-$d_6$) shows absorption bands at 7.20 ppm (multiplet, aromatic hydrogens), 5.80 ppm (multiplet, benzyl hydrogens, C-5 hydrogen and C-3 hydrogens), 5.20 ppm (doublet, C-6 hydrogen), 3.75 ppm (singlet, methoxy hydrogens), 2.35 ppm (singlet, sulfonate methyl hydrogens), 1.70 ppm (singlet, C-2 methyl hydrogens) and 0.85 ppm (singlet, C-2 methyl hydrogens).

PREPARATION J

Reaction of the appropriate 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam compound, chosen from those in Preparations C, D, F, G and H, with p-toluenesulfonic acid monohydrate, according to the procedure of Preparation I, provides the following compounds:

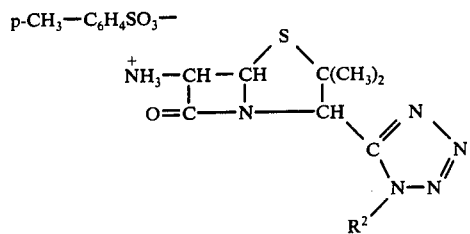

R²

4-hydroxybenzyl
2-hydroxybenzyl
3-chloro-4-hydroxybenzyl
4-hydroxy-3-methylbenzyl
3,4-dihydroxybenzyl
5-methylfurfuryl
2,4-dimethoxybenzyl
2-methoxybenzyl
4-ethoxybenzyl
4-isopropoxybenzyl
4-n-hexyloxybenzyl
4-benzyloxy-3-chlorobenzyl

R²

4-ethoxy-2-fluorobenzyl
3-bromo-4-methoxybenzyl
4-iodo-2-methoxybenzyl
4-isobutoxy-3-methylbenzyl
3,4-di(n-propoxy)benzyl
3-phenyl-4-methoxybenzyl
3,4-dimethylbenzyl
4-n-hexylbenzyl
4-ethoxy-3-phenylbenzyl
5-methylfurfuryl
(2-thienyl)methyl
(5-methyl-2-thienyl)methyl

PREPARATION K

6-Amino-2,2-dimethyl-3-(1-[4-benzyloxybenzyl]tetrazol-5-yl)-penam

A solution consisting of 558 mg. of 6-(triphenylmethylamino)-2,2-dimethyl-3-(1-[4-benzyloxybenzyl]tetrazol-5-yl)penam, 156 mg. of p-toluenesulfonic acid monohydrate and 1 ml. of acetone is stored at ambient temperature for 2.5 hours. It is then added with stirring to 50 ml. of ether. After stirring for a further 10 minutes, the solid which has precipitated is filtered off. This affords 394 mg. of the p-toluenesulfonate of the product. A 304-mg. aliquot of this p-toluenesulfonate salt is dissolved in 10 ml. of methylene chloride, and to the solution is added 69.7 μl. of triethylamine. After 3 minutes, 5ml. of water are added and the mixture is stirred vigorously. The organic phase is then separated off, diluted with ether, dried using anhydrous magnesium sulfate, and evaporated to dryness in vacuo. The residue is 189 mg. (69% yield) of 2-amino-2,2-dimethyl-3-(1-[4-benzyloxybenzyl]tetrazol-5-yl)-penam. The NMR spectrum (in CDCl₃) of the product shows absorption bands at 7.40 ppm (singlet, phenyl hydrogens), 7.15 ppm (quartet, phenylene hydrogens), 5.55 ppm (broad singlet, C-5 and benzyl hydrogens), 5.20 ppm (singlet, C-3 hydrogens), 5.10 ppm (singlet, benzyl hydrogens), 4.60 ppm (doublet, C-6 hydrogen), 1.50 ppm (singlet, C-2 methyl hydrogens) and 0.90 ppm (singlet, C-2 methyl hydrogens).

PREPARATION L

6-Amino-2,2-dimethyl-3-(1-furfuryltetrazol-5-yl) penam

To a stirred solution of 0.422 g. (0.75 mmole) of 6-(triphenylmethylamino)-2,2-dimethyl-3(1-furfuryltetrazol-5-yl)penam in 1 ml of acetone at ambient temperature, is added 0.142 g. (0.75 mmole) of p-toluenesulfonic acid monohydrate. Stirring is continued for 30 minutes, and then the solvent is removed by evaporation in vacuo. This affords the title compound as its p-toluenesulfonate salt. IR (Nujol mull): 1780 cm⁻¹ (B-lactam). NMR (DMSO-d₆): 7.20 ppm (q,4H), 6.40 ppm (m,2H), 5.90 ppm (s,2H), 5.60 ppm (m,2H), 5.00 ppm (d,1H), 2.20 ppm (s,3H), 1.60 ppm (s,3H), 0.80 ppm (s,3H).

PREPARATION M

Preparation of 6-Amino-2,2-dimethyl-3-(5-tetrazolyl)penam From Its p-Toluenesulfonate Salt A two-phase system of 350 ml. of methylene chloride and 250 ml. of deionized water is cooled to 1° C. To this stirred system is then added, portionwise, 100 g. of 6-amino-2,2-dimethyl-3-(5-tetrazolyl)penam p-toluenesulfonate. Concomitant with the addition of the salt, is also added 2 N sodium hydroxide, at a rate sufficient to maintain the pH of the reaction medium in the range from 2.5 to 3.0. The temperature during the addition of the salt is ca. 5° C. At the end of the addition of the salt, the reaction medium is stirred for an additional 3 to 4 minutes at a pH of 3.6. The two-phase system is then separated, and the organic phase is discarded. The pH of the aqueous phase is adjusted to 4.5 (2 N sodium hydroxide), and then the aqueous phase is stored, with stirring, at 3°-5° C. for 1 hour. The precipitate which forms is filtered off, washed with water, and then dried. This gives 29.5 g. (51% yield) of 6-amino-2,2-dimethyl-3-(5-tetrazolyl)penam.

PREPARATION N 6-(D-2-Amino-2-[4-hydroxyphenyl]acetamido)-2,2-dimethyl-3-(5-tetrazolyl)penam To a stirred solution of 0.19 ml. of ethyl chloroformate in 15 ml. of dry acetone, cooled to 0° C., is added 1 drop of N-methylmorpholine, followed by 576 mg. of sodium N-(2-methoxycarbonyl-1-methylvinyl)-D-2-amino-2-(4-hydroxyphenyl)acetate (Long, et al., *Journal of the Chemical Society* [London], Part C, 1920 [1971]). The mixture is stirred for a further 30 minutes, and then it is cooled to about −35° C. To it is then added an ice-cold solution of the sodium salt of 6-amino-2,2-dimethyl-3-(5-tetrazolyl)-penam. The sodium salt solution is prepared by adding 10% sodium hydroxide to a suspension of 436 mg. of 6-amino-2,2-dimethyl-3-(5-tetrazolyl)penam in 5 ml. of water (to give a pH of 7.8), followed by diluting with 25 ml. of acetone. After the addition of the sodium salt solution, the cooling bath is removed, and then the reaction mixture is stirred for a further 30 minutes. At this point, the acetone is removed by evaporation under reduced pressure, and then 20 ml. of methyl isobutyl ketone is added to the aqueous residue. The two-phase system is cooled to 10° C., acidified to pH = 0.9 with dilute hydrochloric acid, and then it is stirred at 10° C. for 1 hour. The methyl isobutyl ketone is separated off and discarded. The pH of the aqueous phase is raised to 6.6, and then it is stored in the refrigerator for 3 hours. The precipitate which forms is filtered off, giving 320 mg. (45% yield) of 6-(D-2-amino-2-[4-hydroxyphenyl]acetamido-2,2-dimethyl-3-(5-tetrazolyl)penam. The infrared spectrum (KBr disc) of the product shows absorptions at 1775 cm$^{-1}$ (β-lactam carbonyl) and 1680 cm$^{-1}$ (amide I band). The NMR spectrum (in DMSO-d$_6$/D$_2$O) shows absorptions at 7.35 and 6.85 ppm (2 doublets, aromatic hydrogens), 5.60 ppm (quartet, C-5 and C-6 hydrogens), 5.10 ppm (multiplet, benzyl hydrogen and C-3 hydrogen), 1.45 ppm (singlet, C-2methyl hydrogens) and 0.95 ppm (singlet, C-2 methyl hydrogens).

PREPARATION O

6-(D-2-Amino-2-[4-hydroxyphenyl]acetamido)-2,2-dimethyl-3-(5-tetrazolyl)-penam, Potassium Salt To a stirred solution of 1.94 g. 6-(D-2-amino-2-[4-hydroxyphenyl]-acetamido)-2,2-dimethyl-3-(5-tetrazolyl)penam in 100 ml. of methanol, cooled to −30° C., is added dropwise 5 ml. of a 1.0N solution of potassium hydroxide in methanol. The mixture is allowed to warm to 0° C., and then it is added dropwise with stirring to 700 ml. of ether. The solid which precipitates is removed by filtration and dried under high vacuum. This affords 1.65 g. (76% yield) of the title potassium salt, m.p. 185° C. (dec.).

When the above procedure is repeated, except that the potassium hydroxide used therein is replaced by an equimolar amount of sodium hydroxide, the product is the sodium salt of 6-(D-2-amino-2-[4-hydroxyphenyl]acetamido)-2-2-dimethyl-3-(5-tetrazolyl)penam.

PREPARATION P

The following ingredients are blended together in the indicated proportions by weight.

| | |
|---|---|
| Calcium carbonate | 17.6 |
| Dicalcium phosphate | 18.8 |
| Magnesium trisilicate | 5.2 |
| Lactose, U.S.P. | 5.2 |
| Potato starch | 0.8 |
| 6-(D-2-Amino-2-[4-hydroxyphenyl]acetamido)-2,2-dimethyl-3-(5-tetrazolyl)penam | 50.0 |

The thoroughly-mixed pharmaceutical composition is filled into soft gelatin capsules, such that each capsule contains 100 mg. of active ingredient.

Capsules are also prepared containing respectively 50 and 500 mg. of active ingredient by varying the proportions of penam compound and excipient blend.

PREPARATION Q

The sodium salt of 6-(D-2-amino-2-[4-hydroxyphenyl]acetamido)-2,2-dimethyl-3-(5-tetrazolyl)penam is thoroughly mixed and ground with sodium citrate (4% by weight). The ground, dry mixture is sterilized and packed into sterile vials, which are then stoppered with serum caps under sterile conditions. When it is intended to use this preparation, sufficient sterile water is injected into the vials to dissolve the contents, and give a solution containing 25 mg/ml of active ingredient. For parenteral use, the solution is withdrawn from the vials using a hypodermic syringe.

In a similar manner, by varying the amount of water added, solutions containing respectively 10, 50, 100 and 200 mg./ml. of active ingredient are prepared.

What is claimed is:

1. A process for the preparation of 6-amino-2,2-dimethyl-3-(5-tetrazolyl)penam, or an acid-addition salt thereof, which comprises reacting a compound of formula

[structure: $R^1$—NH—CH—CH linked to S—C(CH$_3$)$_2$, O=C—N—CH, with tetrazolyl ring bearing $R^2$]

or an acid-addition salt thereof, with hydrogen fluoride, at a temperature within the range from about −20° C. to about 20° C.;

wherein
$R^1$ is selected from the group consisting of hydrogen and

[structure: triphenylmethyl group with substituents $R^3$, $R^4$, $R^5$ on the three phenyl rings]

wherein
$R^3$, $R^4$, and $R^5$ are each selected from the group consisting of hydrogen, fluoro, chloro, bromo, alkyl having from one to four carbon atoms, alkoxy having from one to four carbon atoms and phenyl;
and $R^2$ is selected from the group consisting of

[structures: —CH$_2$—phenyl with $R^7$, $R^8$ substituents, and —CH$_2$—heterocycle with X and $R^{10}$]

wherein
$R^7$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, benzyloxy and phenyl;
$R^8$ is selected from the group consisting of hydrogen, hydroxy, fluoro, chloro, unbranched-alkyl having from one to six carbon atoms and unbranched-alkoxy having from one to six carbon atoms;
$R^{10}$ is selected from the group consisting of hydrogen and methyl;
and X is selected from the group consisting of oxygen and sulfur;
provided that at least one of $R^7$ and $R^8$ is selected from the group consisting of 2-hydroxy, 4-hydroxy, 4-alkoxy having from one to six carbon atoms, 2-(unbranched-alkoxy) having from one to six carbon atoms and 4-benzyloxy.

2. The process according to claim 1, wherein at least about twenty molar equivalents of hydrogen fluoride are used.

3. The process according to claim 2, wherein the said temperature is in the range from about −5° C. to 5° C.

4. The process according to claim 3, wherein $R^1$ is triphenylmethyl.

5. The process according to claim 3, wherein $R^1$ is hydrogen.

6. The process according to claim 5, wherein $R^2$ is furfuryl.

7. The process according to claim 5, wherein $R^2$ is

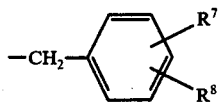

8. The process according to claim 7, wherein $R^7$ is hydrogen and $R^8$ is 4-alkoxy having from one to six carbon atoms.

9. The process according to claim 8, wherein $R^8$ is 4-methoxy.

10. The process according to claim 1 wherein the action is carried out in the presence of at least one molar equivalent of anisole.